(12) United States Patent
Werner et al.

(10) Patent No.: US 9,060,811 B2
(45) Date of Patent: Jun. 23, 2015

(54) PEDICLE-SCREW ASSEMBLY

(75) Inventors: Claudia Werner, Neu-Ulm (DE); Stefan Midderhoff, Ulm (DE)

(73) Assignee: ULRICH GMBH & CO.KG, Ulm (DE)

( * ) Notice: Subject to any disclaimer, the term of this patent is extended or adjusted under 35 U.S.C. 154(b) by 50 days.

(21) Appl. No.: 13/296,276

(22) Filed: Nov. 15, 2011

(65) Prior Publication Data

US 2012/0123486 A1 May 17, 2012

(30) Foreign Application Priority Data

Nov. 15, 2010 (DE) .......... 10 2010 060 555

(51) Int. Cl.
*A61B 17/70* (2006.01)

(52) U.S. Cl.
CPC ......... *A61B 17/7037* (2013.01); *A61B 17/7038* (2013.01); *A61B 17/7035* (2013.01)

(58) Field of Classification Search
CPC ........... A61B 17/7035; A61B 17/7037; A61B 17/7038
USPC ................. 606/246–279, 300–321
See application file for complete search history.

(56) References Cited

U.S. PATENT DOCUMENTS

| | | | |
|---|---|---|---|
| 6,454,772 B1 | 9/2002 | Jackson | |
| 8,012,183 B2 | 9/2011 | Alain | |
| 2005/0187548 A1* | 8/2005 | Butler et al. | 606/61 |
| 2005/0203516 A1 | 9/2005 | Biedermann | |
| 2007/0118117 A1* | 5/2007 | Altarac et al. | 606/61 |
| 2007/0118123 A1* | 5/2007 | Strausbaugh et al. | 606/61 |
| 2007/0288004 A1 | 12/2007 | Alvarez | |
| 2009/0062861 A1 | 3/2009 | Frasier et al. | |
| 2009/0076552 A1* | 3/2009 | Tornier | 606/264 |
| 2009/0105716 A1 | 4/2009 | Barrus | |
| 2010/0228293 A1 | 9/2010 | Courtney | |
| 2011/0257690 A1* | 10/2011 | Rezach | 606/302 |

\* cited by examiner

*Primary Examiner* — Jerry Cumberledge
*Assistant Examiner* — Nicholas Plionis
(74) *Attorney, Agent, or Firm* — Andrew Wilford

(57) ABSTRACT

A pedicle-screw assembly has a screw having a threaded shaft extending along a screw axis and having a ball head. A body extending along a body axis is formed with an axially inwardly open screw-head seat in which the ball head can fit and with an oppositely axially outwardly open rod seat. A retainer fitted in the screw-head seat engages around the ball head and in the screw-head seat, and at least one pin extends radially of the body axis and seated in both the body and the retainer for pivoting of the retainer in the screw-head seat about a retainer axis substantially perpendicular to the body axis between a position with the body axis coaxial with the screw axis and a position with the body axis forming an acute axially outwardly open angle with the screw axis. The ball head is swivelable in the retainer.gget

13 Claims, 5 Drawing Sheets

PEDICLE-SCREW ASSEMBLY

FIELD OF THE INVENTION

The present invention relates to a pedicle-screw assembly. More particularly this invention concerns such an assembly used to anchor a stabilizing rod to spinal vertebrae.

BACKGROUND OF THE INVENTION

A typical pedicle-screw assembly is used in implants for correcting and stabilizing the spinal column. Such an assembly has a screw that is anchored in vertebral bone and has a screw head at an axial end of a threaded shaft. A tulip head or body has a screw-head seat open toward the threaded shaft for the screw head and a rod seat formed between the flanks or wings of the tulip body for fixing a spine-stabilizing rod.

A pedicle-screw assembly of this type is known from US 2007/0288004. It has a threaded shaft that can be deflected polyaxially by a maximum of 45° relative to the longitudinal tulip body axis, and an seat for the screw head that is formed by flexible fingers that grip over the equator of the ball-shaped screw head. As a result, the ball-shaped screw head is retained by being concentrically clamped with respect to the longitudinal head axis.

In US 2010/065648 a similar pedicle-screw assembly is shown that also forms a snap lock for retaining the ball-shaped screw head. The fingers reach over the equatorial line of the ball-shaped head, as a result of which polyaxial deflection by a maximum of 45° of the threaded shaft is possible relative to the longitudinal tulip body axis.

US 2005/0203516 shows a pedicle-screw assembly that can hold a rectangular-section rod. In one embodiment, the threaded shaft can be separated from the head, and the head is mounted in the threaded shaft radial to the longitudinal head axis. A slot allows deflection of the threaded shaft to the head around the longitudinal head axis. This relative rotation is intended to protect the screw from being screwed out of the bone of the spinal cord when the rod is tightened. Even here, no deflection of the threaded shaft of more than 45° is possible.

To be able to perform spinal fixation efficiently, it is necessary to deflect the threaded shaft polyaxially relative to the longitudinal head axis in order to be able to attach the rod that will later anchor the vertebrae securely at the pedicle-screw assemblys. The threaded shaft of the pedicle screw is usually screwed into the massive part of the bone, as a result of which expensive steps for bone regeneration can be avoided. The threaded shafts of the pedicle screws that are used are therefore often screwed into bones at different positions or at different angles. As a result, a displaceable the tulip body is very helpful for fixing the rod that is connecting the bones firmly and securely at the head of the pedicle screw.

OBJECTS OF THE INVENTION

It is therefore an object of the present invention to provide an improved pedicle-screw assembly.

Another object is the provision of such an improved pedicle-screw assembly that overcomes the above-given disadvantages, in particular in which the threaded shaft can be deflected further relative to the longitudinal axis head axis than in known pedicle-screw assemblys.

SUMMARY OF THE INVENTION

A pedicle-screw assembly has according to the invention a screw having a threaded shaft extending along a screw axis and having a ball head at an axially outer end. A body extending along a body axis is formed with an axially inwardly open screw-head seat in which the ball head can fit and with an oppositely axially outwardly open rod seat adapted for holding a spine-stabilizing rod. A retainer fitted in the screw-head seat engages around the ball head and in the screw-head seat, and at least one pin extends radially of the body axis and seated in both the body and the retainer for pivoting of the retainer in the screw-head seat about a retainer axis substantially perpendicular to the body axis between a position with the body axis coaxial with the screw axis and a position with the body axis forming an acute axially outwardly open angle with the screw axis. The ball head is swivelable in the retainer.

The pedicle-screw assembly wherein the ball head has a substantially spherical outer surface from which the threaded shaft extends and that has an equator lying in a plane perpendicular to the screw axis. The retainer engaging around the ball head least mostly between the equator and the shaft. This equator defines a plane and the retainer axis is generally in the plane. The retainer engaging the ball head axially outward of the retainer axis.

This embodiment of the pedicle-screw assembly according to the invention offers the advantage that the head in the head retainer can be deflected by a maximum of 45° relative to the longitudinal head axis, and that a further deflection is made possible by the rotatable mounting of the head retainer. Thus it can be swung into a position in which it would come out of the screw-head seat if it were not for the interposition of the pivotal retainer between the tulip body and the screw head.

It is thereby of advantage when the head retainer is rotatably mounted on two pivot pins rotatable in respective pin bores, as this way a secure mounting of the head retainer in the tulip body is ensured, and head retainer is prevented from falling out of the tulip body.

A further advantageous embodiment is that the pin bores are open toward the threaded shaft. Thus, the head retainer can be inserted, during the hereby facilitated assembly of the pedicle screw into the tulip body from the top, in order to detachably connect the pin bores with the pivot pins.

Moreover, it is of advantage when the head retainer has an opening having a V-shaped curve in section toward the threaded shaft that is perpendicular to a bearing axis formed by the two pivot pins. Here, the head retainer can retain the ball-shaped head saucer-like in the tulip body from the bottom. While the retainer of US 2007/0288004 of US 2010/065648 and US 2005/0203516 surround the head from the side directed away from the threaded shaft, the engagement from below, namely from the side closer to the threaded shaft, prevents the head and the tulip body from detaching from each other due to active tensile forces.

A further advantage is that the threaded shaft can be deflected polyaxially relative to the longitudinal tulip body axis. This ensures that the threaded shaft can not only be deflected along the direction of pivoting, but also in any other desired direction. Thus, easier fitting of the rod to the tulip body is possible.

A further advantage is that the tulip body has at least one cutout into which fits the screw shaft at its end close to the head. This way, extended deflection of the threaded shaft is possible relative to the longitudinal head axis, as it is only blocked in its further deflection by the cutout. Accordingly, the geometry of the tulip body and the head retainer are the limiting elements for deflecting the threaded shaft relative to the longitudinal head axis. If the cutout is oriented 90° offset from to the bearing axis, the threaded shaft can first be deflected by the pivoting of the head retainer, subsequently by the sliding motion of the head in the head retainer, so that an increased deflection of the threaded shaft relative to the longitudinal axis of the head is made possible.

It is also advantageous when the threaded shaft can be deflected in a first direction relative to the longitudinal head axis by a pivoting motion of the head retainer, and a sliding motion of the head in the head retainer is deflectable by a larger angle than in a second direction by only a sliding motion of the head in the head retainer. As a result, the tulip body can be attached to the head in such a way that it can be tipped further in a first direction in order to be able to mount the stabilizing rod properly in the rod seat, when the threaded shaft is, for example, particularly steep, namely at a large angle to the normal surface in which the screw is to be fixed and anchored in the bone.

If this first direction is perpendicular to the bearing axis of the head retainer, it offers the advantage that here too, pivoting of the head retainer and sliding of the head in the head retainer can be in the first direction relative to the two deflection angles. It is thereby advantageous when the threaded shaft in the first direction is deflectable to a maximum of 61°, and in the second direction to a maximum of 45°. From this, dimensions for the threaded shaft, the head holder and the tulip body follow, which have very high stability and are additionally formed sufficiently small so that they do are not bothersome for the patient.

A further advantageous embodiment is that the tulip body has bores radial to the longitudinal axis of the tulip body. These bores make fitting the pivot pins for pivoting of the head retainer easier in the tulip body. Thus, the pivot pins can easily be slid radially to the longitudinal head axis into the tulip body from the outside. Moreover, by using these bores, additional components can be secured in the tulip body, so advantageously a clamping piece can be secured in the tulip body by at least one locking pin. This clamping piece prevents the tulip body from sliding over the threaded shaft. Moreover, it serves to guide the ball-shaped head in the tulip body. If the clamping piece has a tool guide, it provides the advantage that the threaded shaft can be screwed in using the head and a tool fitted through the tool guide to anchor it in the bone.

Moreover, it is advantageous that the tulip body has at an axial spacing from the end holding the rod at least one guide groove. As a result, additional accessories such as, for example, a percutaneous sleeve, can be fastened at the tulip body to align it for fitting with the rod.

It is also advantageous when the tulip body is designed with a tapered outer diameter in its axial extension.

For the fixation of the rod in the rod seat it is advantageous when at the inner surface of the end of the flanks holding the rod is provided with a spindle thread. Thus, a screw can be screwed into the tulip body to fix the rod in the tulip body on the head.

BRIEF DESCRIPTION OF THE DRAWING

The above and other objects, features, and advantages will become more readily apparent from the following description, reference being made to the accompanying drawing in which.

DETAILED DESCRIPTION

Figure 1:
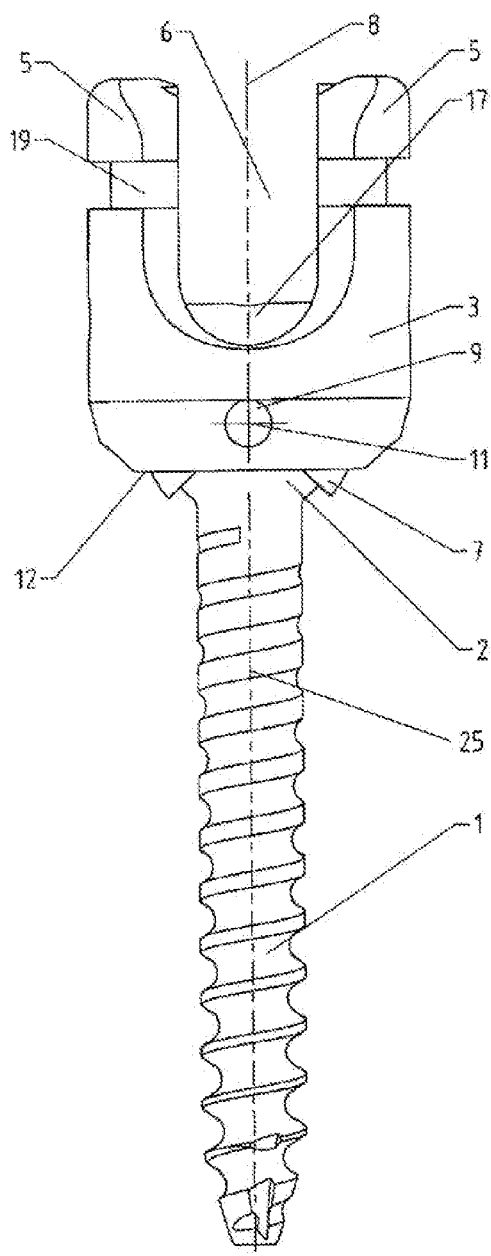
FIG. 1 is a side view of the pedicle-screw assembly in a first direction.

As seen in FIG. 1 a pedicle-screw assembly according to the invention has a screw 1, 2 having a shaft 1 extending along a screw axis 25 and a tulip body 3 centered on a longitudinal body axis 8 that in FIGS. 1-4 and 7 is coaxial with the screw axis 25. The body 3 forms an axially inwardly (downward in FIGS. 1-4) open head seat 4 and an axially outwardly open rod seat 6, both centered on the body axis 8. A head retainer 7 is mounted via pivot pins 9 extending radial to the longitudinal head axis 8 in the head seat 4 of the tulip body 3. The head retainer 7 thus can pivot in the seat about a bearing axis 11 formed by the two pivot pins 9 and extending perpendicularly through the axis 8. This retainer 7 is V-shaped axially outward toward the screw shaft 1. In addition, a clamping piece 17 is provided in the between the seats 4 and 6 tulip body 3.

Figure 2:
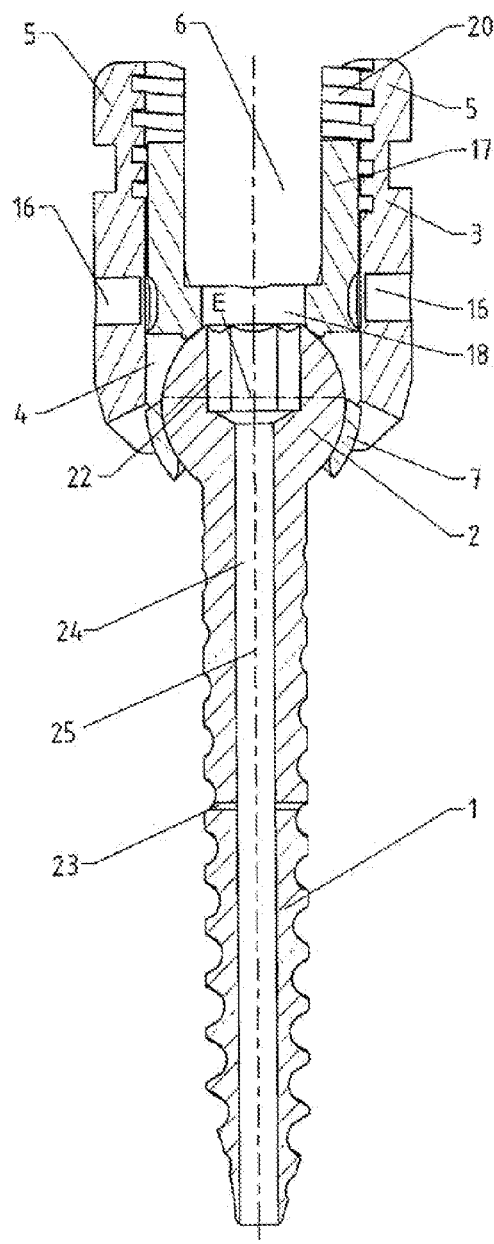
FIG. 2 is a longitudinal section through the pedicle-screw assembly viewed in the first direction.

FIG. 2 shows how a head 2 of the screw 1, 2 is retained in the tulip body 3 from below by the head retainer 7. A clamping piece 17 forms a tool guide passage 18 centered on the axis 8 and the screw head 2 forms a tool seat 22, here a hex seat, so that a tool fitted through the sleeve-like body 3 and through the passage 18 can be used to screw in the screw 1, 2. Moreover, the screw shaft 1 is formed with radial bores 23 (only two shown) in its outer surface and an axial passage 24 for filling in strengthening material is shown.

The clamping piece 17 is locked in the tulip body 3 via bores 16, and this body 3 has an internal screw thread 20 for securing the rod that is to be inserted later. To this end an unillustrated stabilizing rod is laid transversely in the outer seat 6 between the wings 5 of the body and an unillustrated nut is threaded into the screwthread 20 to press it down against the clamping body 17 and to in turn press the clamping body against the ball head 2, as is well known in the art. A guide groove 19 is provided at an axial spacing from the outer body end where the unillustrated rod is held between the wings 5.

Figure 3:
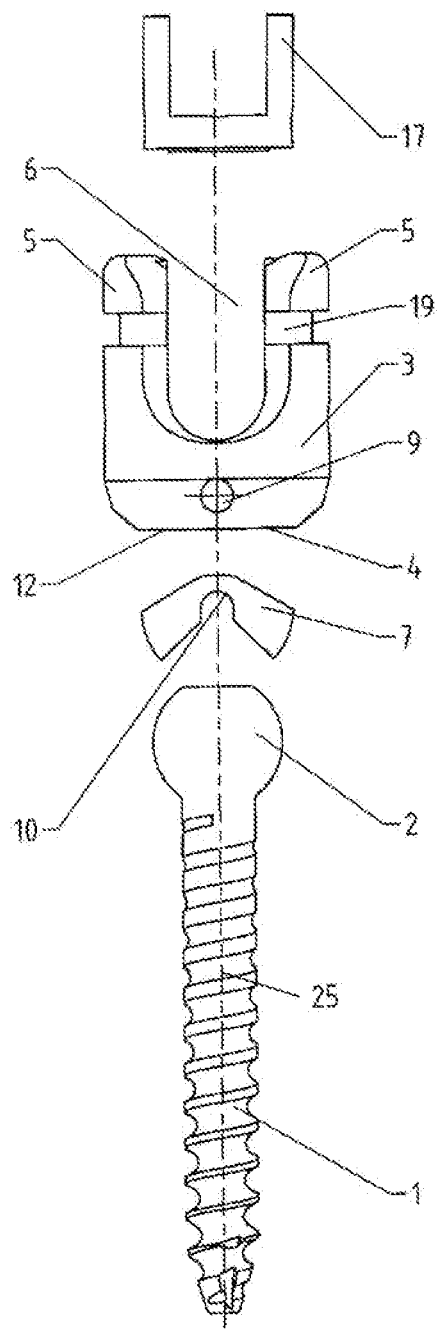
FIG. 3 is an exploded view of the pedicle-screw assembly viewed in the first direction.

FIG. 3 is a view exploded along the head axis 8 of the pedicle screw 1, 2, here showing the bores 16 for inserting pins into the tulip body 3. The head retainer 7 has two pin seats 10 and its V-shape can be seen clearly.

Figure 4:
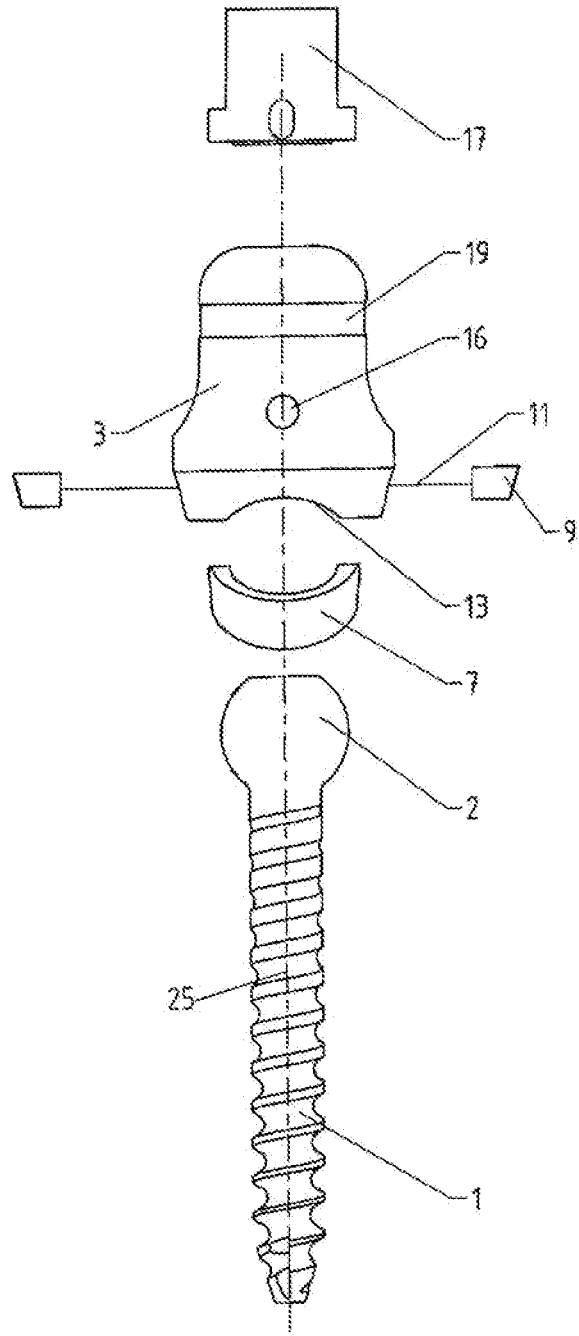
FIG. 4 is an exploded view of the pedicle-screw assembly viewed in a second direction.

FIG. 4 shows the FIG. 3 view rotated by 90° about the head axis 8, and here the tulip body 3 is shown to have an axially outwardly tapered shape. Moreover, part-circular cutouts 13 in which the screw shaft 1 can fit are shown. These cutouts 13 diametrally flank the axis 8 and open axially inwardly and have part-cylindrical edge faces centered on axes that here meet the axis 8 at an acute angle of 61° and are of the same radius of curvature as the screw shaft 3 immediately adjacent the ball head 2.

Figure 5A:
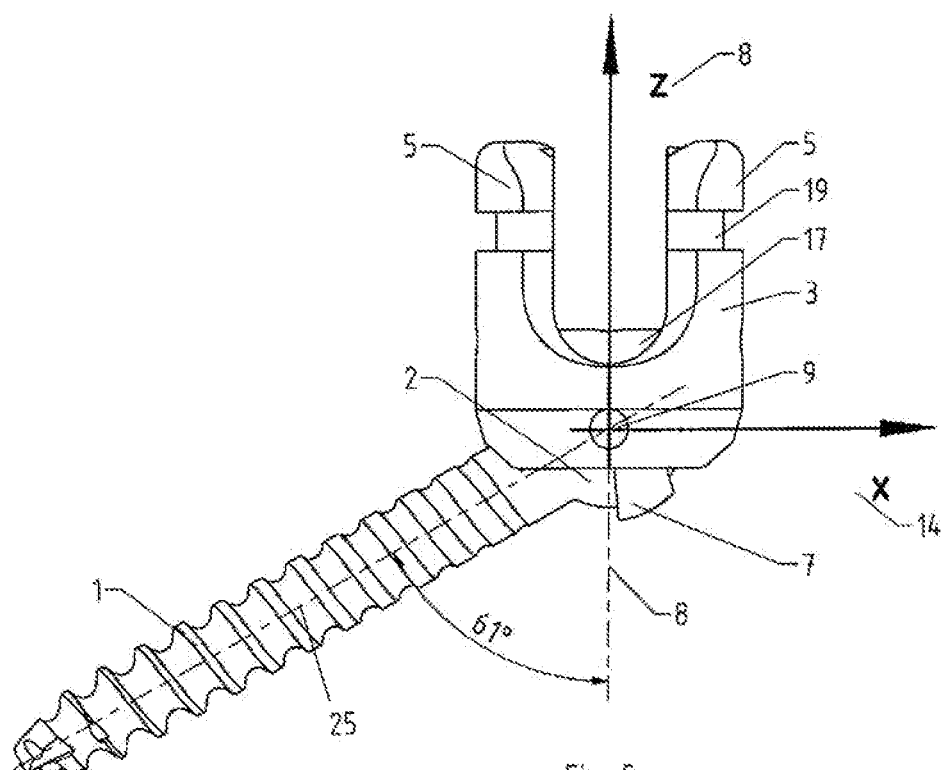
FIG. 5a is a side view of the pedicle-screw assembly with a deflected shaft viewed in the first direction.
Figure 5B:
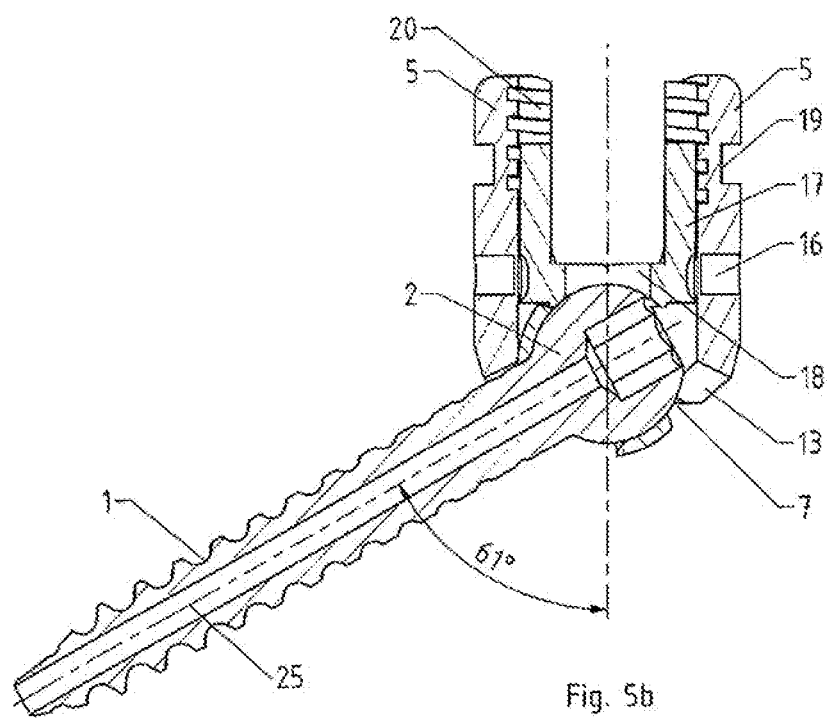
FIG. 5b is a longitudinal section through the pedicle-screw assembly with a deflected shaft viewed in the first direction.

When moving into the position of FIGS. 5a and 5b in a first direction 14 perpendicular to a plane defined the body axis 8 and retainer axis 11, the retainer 7 engages the inner face of the piece 17 when the axes 25 and 8 form an angle of about 45° and cannot be pivotally deflected any further. The screw head 2 can however then slide or swivel in the head retainer 7 and move further into the end position of FIGS. 5a and 5b with the screw axis 25 extending at 61° to the body axis 8 and the shaft 2 fitted to one of the cutouts 13.

Figure 6A:
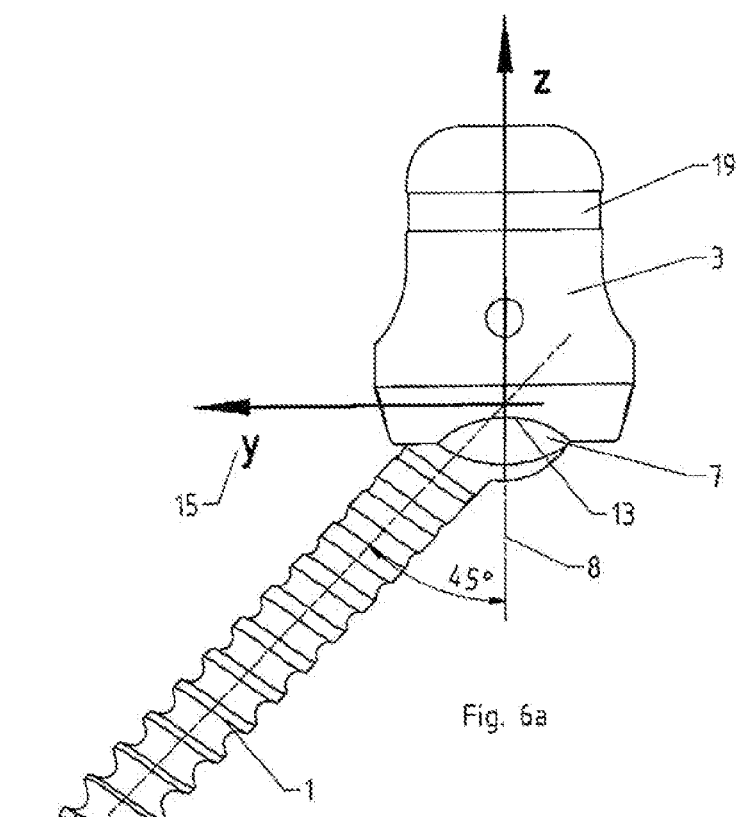
FIG. 6a is a side view of the pedicle-screw assembly with a deflected screw shaft viewed in the second direction
Figure 6B:
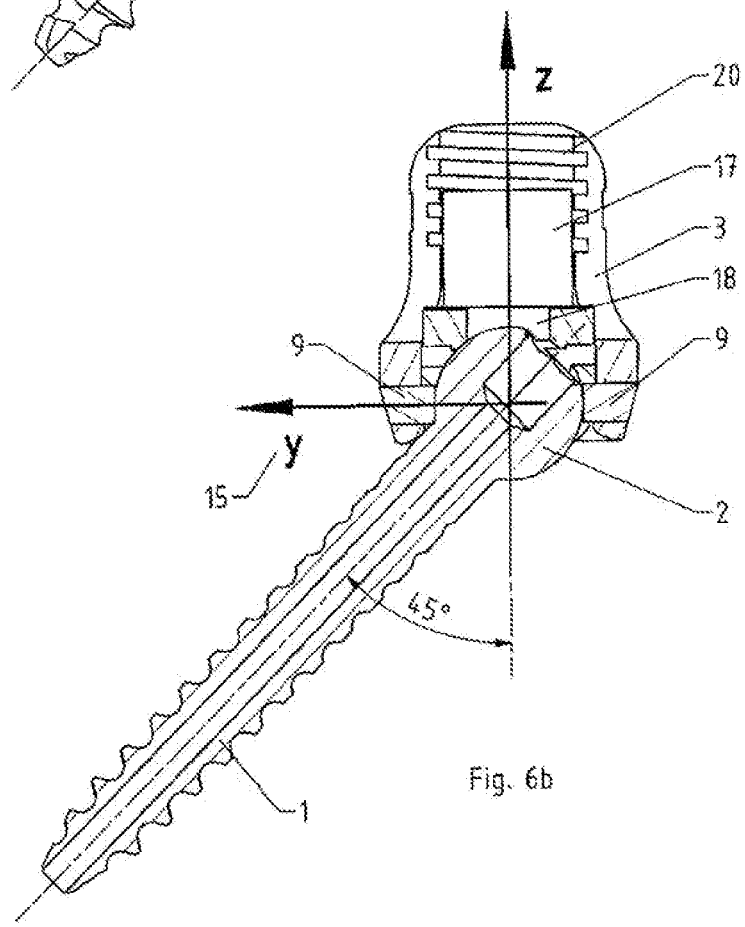
FIG. 6b is a longitudinal section through the pedicle-screw assembly with a deflected screw shaft viewed in the second direction.

If, instead as shown in FIGS. 6a and 6b, the shaft 1 does not swing to fit into one of the cutouts 13, but pivots in a direction 16 parallel to a plane including the axis 8 and perpendicular to the axis 11, the pivot angle is limited to 45° when in a position engaging the inner edge of the body 3 in which further deflection is impossible. When in this position the screw 1, 2 can be swiveled about the point where the axes 6, 11, and 25 meet to fit it into one of the cutouts 13, if necessary, and allow the angle to be increased.

Thus with the inventive system the retainer 7 between the spherical ball head 2 and the complementary head seat 4 serves for holding the screw 1, 2 in place even when in an angular position in which it otherwise would slip out of the seat 4. This is possible because at least in the coaxial position of FIGS. 1-4 and 7 the retainer wraps around the ball head 2 below its equator E, which extends through the center of this ball head 2 and which also includes the axis 11. When the screw 1, 2 moves into an extremely deflected end position as shown in FIGS. 6a and 6b the one semicircular part 13 of the retainer 7 actually engages right under the ball head 2 to do its job of retaining the ball head 2 in the seat 2.

The drawing shows the embodiment with the advantageous dimensions of the individual components of the pedicle-screw assembly, as a result of which a deflection angle of 45° is achievable in the second direction according to FIG. 6a.

Figure 7:
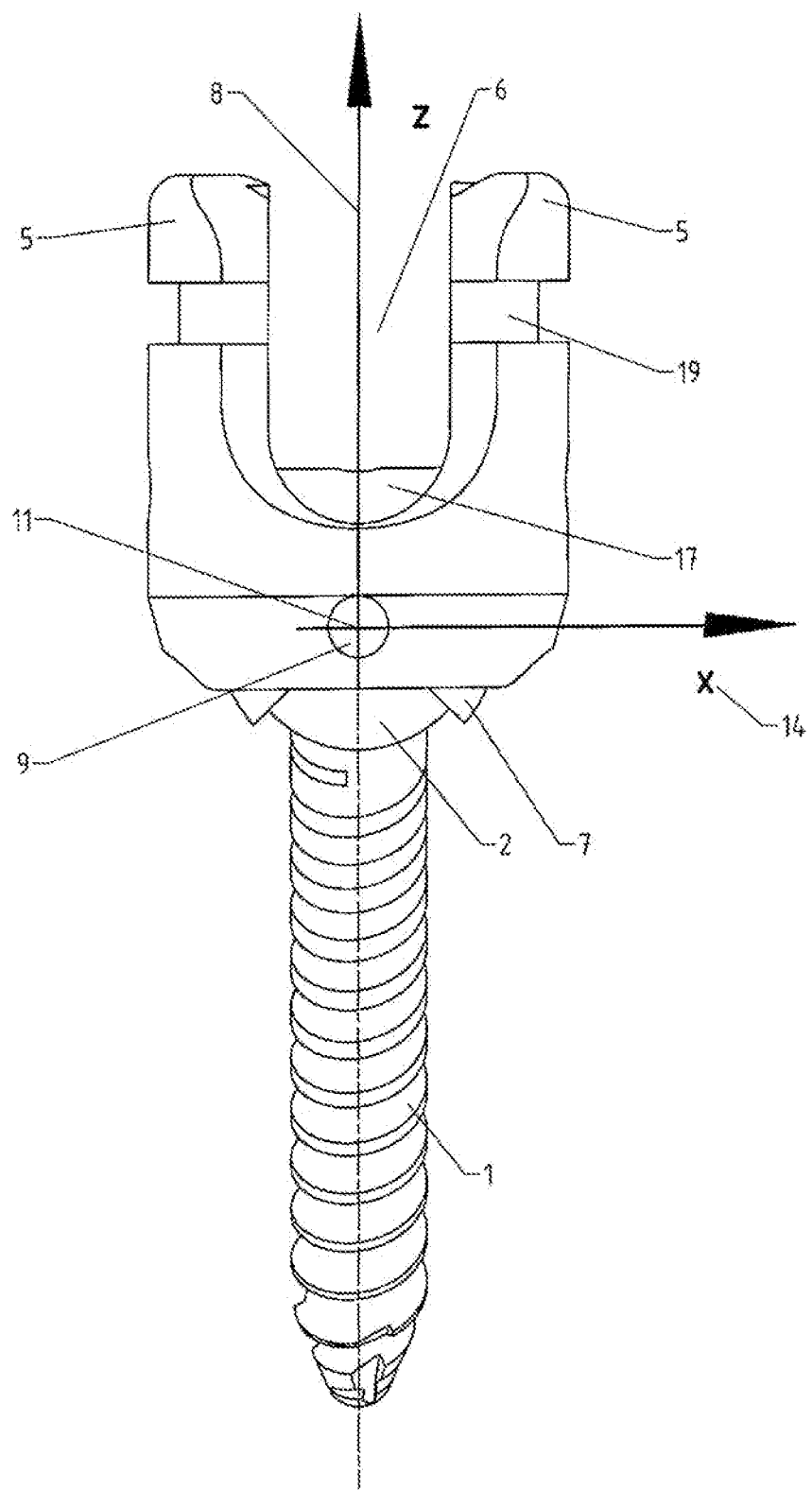
FIG. 7 is a view along the longitudinal axis of the tulip body like FIG. 6a but rotated by 90°.

FIG. 7 shows a view of FIGS. 6a and 6b taken on the head axis 8 rotated by 90°, where here it is once again shown that deflection of the screw shaft 1 takes place parallel to the bearing axis 11.

We claim:

1. A pedicle-screw assembly comprising:
   a screw having a threaded shaft extending along a screw axis and having at an axially outer end of the shaft a ball head having a substantially spherical outer surface from which the threaded shaft extends and an equator lying in a plane perpendicular to the screw axis;
   a tulip body extending along a body axis and formed with an inwardly open screw-head seat in which the ball head can fit, with two pin seats open radially inwardly of the body axis into the screw-head seat, and with an oppositely outwardly open rod seat adapted for holding a spine-stabilizing rod;
   a retainer fitted in the screw-head seat and engaging around the spherical outer surface of the ball head mostly between the equator and the shaft; and
   respective pins extending radially of the body axis and seated in the pin seats of the body and in the retainer for pivoting of the retainer in the screw-head seat about a retainer axis substantially perpendicular to the body axis between a position with the body axis coaxial with the screw axis and a position with the body axis forming an acute outwardly open angle with the screw axis, the ball head being swivelable in and relative to the retainer.

2. The pedicle-screw assembly defined in claim 1, wherein the pins diametrally flank the screw head.

3. The pedicle-screw assembly defined in claim 1, wherein the retainer is V-shaped and opens inward toward the screw shaft.

4. The pedicle-screw assembly defined in claim 1, wherein the retainer has a substantially spherical inner surface complementary to the substantially spherical outer surface of the ball head, both surfaces being centered on a substantially common point about which the screw is swivelable polyaxially in the retainer.

5. The pedicle-screw assembly defined in claim 1, wherein the body is formed at an axial inner end with an inwardly open cutout in which the screw shaft can fit in an end position.

6. The pedicle-screw assembly defined in claim 5, wherein, when the screw shaft is deflected to fit into the cutout, an angle between the body axis and the screw axis is greater than when the screw shaft is deflected into axial contact with an axial inner end of the body outside the cutout.

7. The pedicle-screw assembly defined in claim 6, wherein, when the screw shaft is engaged in the cutout, the angle is at most 61° and, when the screw shaft is engaged with a body edge outside the cutout, the angle is at most 45°.

8. The pedicle-screw assembly defined in claim 1, wherein the pin seats open radially outwardly of the body axis.

9. The pedicle-screw assembly defined in claim 1, further comprising:
   a clamping piece located between the screw-head seat and the rod seat and defining faces of both of the screw-head and rod seats.

10. The pedicle-screw assembly defined in claim 9, wherein the clamping piece has a throughgoing guide passage on the body axis and through which a tool can pass and the screw head is formed with a seat open axially along the screw axis, alignable with the guide passage, and shaped to complementarily receive the tool.

11. The pedicle-screw assembly defined in claim 1, wherein the body is formed with at least one annular and radially outwardly open groove spaced outwardly of the retainer axis.

12. The pedicle-screw assembly defined in claim 1, wherein the body tapers outward.

13. The pedicle-screw assembly defined in claim 1, wherein an inner surface of the rod seat is formed at an outer end of the rod seat with a screwthread.

* * * * *